United States Patent
Kano et al.

(10) Patent No.: US 10,925,839 B2
(45) Date of Patent: *Feb. 23, 2021

(54) COMPOSITION FOR TREATING JOINT DISEASE AND KIT CONTAINING SAME

(71) Applicant: SEIKAGAKU CORPORATION, Tokyo (JP)

(72) Inventors: Kazuyuki Kano, Tokyo (JP); Yuji Nobuoka, Tokyo (JP); Takayuki Seo, Tokyo (JP)

(73) Assignee: SEIKAGAKU CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/492,365

(22) PCT Filed: Mar. 14, 2018

(86) PCT No.: PCT/JP2018/009945
§ 371 (c)(1),
(2) Date: Sep. 9, 2019

(87) PCT Pub. No.: WO2018/168921
PCT Pub. Date: Sep. 20, 2018

(65) Prior Publication Data
US 2020/0352882 A1   Nov. 12, 2020

(30) Foreign Application Priority Data

Mar. 14, 2017 (JP) .............................. JP2017-049204
Jul. 6, 2017 (JP) .............................. JP2017-132510

(51) Int. Cl.
| | | |
|---|---|---|
| *A61K 31/136* | (2006.01) | |
| *A61K 47/55* | (2017.01) | |
| *A61P 19/02* | (2006.01) | |
| *A61K 9/00* | (2006.01) | |
| *A61K 31/728* | (2006.01) | |

(52) U.S. Cl.
CPC .......... *A61K 31/136* (2013.01); *A61K 9/0019* (2013.01); *A61K 31/728* (2013.01); *A61K 47/55* (2017.08); *A61P 19/02* (2018.01)

(58) Field of Classification Search
None
See application file for complete search history.

(56) References Cited

U.S. PATENT DOCUMENTS

| | | |
|---|---|---|
| 2008/0221062 A1 | 9/2008 | Miyamoto et al. |
| 2016/0151506 A1 | 6/2016 | Miyamoto et al. |

FOREIGN PATENT DOCUMENTS

| | | |
|---|---|---|
| CN | 1930190 | 4/2011 |
| EP | 1 082 963 | 3/2001 |
| JP | 2016-156029 | 9/2016 |
| WO | 99/59603 | 11/1999 |
| WO | 2005/066214 | 7/2005 |
| WO | 2015/005458 | 1/2015 |

OTHER PUBLICATIONS

Pereira, Duarte et al., "Potential role of age, sex, body mass index and pain to identify patients with knee osteoarthritis", International Journal of Rheumatic Diseases, vol. 20, 2017, pp. 190-198.
Weiss, Elizabeth, "Knee osteoarthritis, body mass index and pain: data from the Osteoarthritis Initiative", Rheumatology, vol. 53, Jun. 14, 2014, pp. 2095-2099.
Sudo, Akihiro et al., "Prevalence and risk factors for knee osteoarthritis in elderly Japanese men and women", Journal of Orthopaedic Science, vol. 13, May 12, 2008, pp. 413-418.
Official Communication issued in International Bureau of WIPO Patent Application No. PCT/JP2018/009945, dated Jun. 5, 2018.
Official Communication dated Jun. 5, 2018 in International Application No. PCT/JP2018/009945 (ISR).
Official Communication dated Jun. 5, 2018 in International Application No. PCT/JP2018/009945 (IPRP).

*Primary Examiner* — Layla D Berry
(74) *Attorney, Agent, or Firm* — Greenblum & Bernstein, P.L.C.

(57) ABSTRACT

The present invention pertains to a composition for treating joint diseases and a kit including the same, and the purpose of the present invention is to provide a composition for treating joint diseases which can be used in patients with joint diseases, and a kit which includes the same. Specifically provided is a composition for treating joint diseases that obtains higher efficacy than prior preparations by means of a composition for treating joint diseases which includes a modified hyaluronic acid having a group derived from an anti-inflammatory compound or a pharmaceutically acceptable salt of the modified hyaluronic acid, and which is targeted at patients with human joint diseases who have a BMI of 25 kg/m$^2$ or higher.

16 Claims, No Drawings

COMPOSITION FOR TREATING JOINT DISEASE AND KIT CONTAINING SAME

TECHNICAL FIELD

The present invention relates to a composition for treating joint disease, and to a kit containing the composition.

BACKGROUND ART

As society continues to age, osteoarthritis (hereinafter, also referred to as "OA"), a dysfunction due to joint pain and join degeneration, becomes one of the most common joint disease worldwide, and is one of the principal causes of physical impairment that interferes with daily living in the elderly. Moreover, rheumatoid arthritis (hereinafter, also referred to as "RA") has been also known as a form of polyarthritis accompanied by joint swelling and pain. In the case of RA, if the disease progress over a long period of time, degeneration or deformation of cartilages and bones may also occur as cartilages and bones are destroyed, restricting the range of joint movement and otherwise causing physical impairment that interferes with daily living.

At present, preparations using hyaluronic acid and its derivatives are used as drugs for joint disease including osteoarthritis and rheumatoid arthritis. Hyaluronic acid preparations are normally formulated as injections, and administered directly to the affected joints such as knee and shoulder joints with the aim of suppressing pain and improving dysfunction due to joint disease through the lubricating action, impact absorbing action and cartilage metabolism improving action of hyaluronic acid. Commercial hyaluronic acid preparations include those containing purified sodium hyaluronate as an active ingredient (such as ARTZ® and SUVENYL®. With these preparations, three to five continuous administrations at a rate of one per week are considered necessary.

Preparations containing crosslinked hyaluronan as an active ingredient include those (such as SYNVISC®) requiring three continuous administrations at a rate of one per week, as well as single-administration preparations (such as SYNVISC-ONE®, GEL-ONE® and MONOVISC®) with which treatment is completed in a single administration.

Meanwhile, steroids and non-steroidal anti-inflammatory compounds has been known as immediate-acting drugs, and has been also used for treatment aimed at alleviating joint pain caused by OA and RA and the like. For example, triamcinolone acetonide is a steroid that is used to treat joint disease including rheumatoid arthritis. Triamcinolone acetonide is commercially available as a drug for intra-articular cavity injection, and treatment requires administration every one to two weeks. In the case of non-steroidal anti-inflammatory compounds, ointments and orally administered agents containing diclofenac sodium as an active ingredient has been known for example.

Mixtures or conjugates of hyaluronic acid or its derivatives with steroids or non-steroidal anti-inflammatory compounds has been also known as active ingredients. For example, a mixture (CINGAL®) of crosslinked hyaluronic acid and triamcinolone hexacetonide has been formulated as a drug for single administration. Some compounds containing hyaluronic acid or its derivatives linked to steroids or non-steroidal anti-inflammatory compounds has been also known. For example, Patent Literature 1 and Patent Literature 2 describe derivatives containing anti-inflammatory compounds introduced into hyaluronic acid via spacers. These are aimed at achieving both immediate pain relief and long-term pain relief through functional improvement. However, adequate methods for treating OA and PA have not yet been established or provided.

CITATION LIST

[Patent Literature]
  Patent Literature 1: WO 2005/066214
  Patent Literature 2: Japanese Patent Application Publication No. 2016-156029

SUMMARY OF INVENTION

It is an object of the present invention to provide a highly effective composition for treating human joint disease patients.

After exhaustive research into the above problems, the inventors have completed the present invention after discovering unexpectedly that a composition for treating joint disease containing a modified hyaluronic acid or a pharmaceutically acceptable salt thereof having a group derived from an anti-inflammatory compound has an especially excellent improvement effect when administered to a particular patient group among patients with joint diseases, and that the above problems could be solved with this composition for treating joint disease. More specifically, the problems have been solved by using a group of joint disease patients with a body mass index (hereunder called "EMI" in this Description) of at least 25 $kg/m^2$ as the target patient group for administration.

One aspect of the invention relates to a composition for treating joint disease, containing a modified hyaluronic acid or a pharmaceutically acceptable salt thereof having a group derived from an anti-inflammatory compound, for treating a human joint disease patient with a specified BMI. Another aspect of the present invention relates to a method for treating human joint disease, including a step of administering this composition for treating joint disease into a joint of a patient requiring it and having a specified BMI. A specified BMI here means a BMI of at least 25 $kg/m^2$ for example. Yet another aspect of the present, invention relates to a kit containing the composition for treating joint disease. This kit includes, for example as one constituent element, a syringe including the composition packed in a syringe barrel.

More particularly, the present invention relates to [1] to [5] below.

[1] A composition for treating joint disease, containing a modified hyaluronic acid or a pharmaceutically acceptable salt thereof having a group derived from a steroidal or non-steroidal anti-inflammatory compound, for treating a human joint disease patient having a BMI of at least 25 $kg/m^2$.

[2] A kit containing a syringe containing the composition according to [1] above packed in a syringe barrel.

[3] A composition for use in a method for treating joint disease of human joint disease patients, containing a modified hyaluronic acid or a pharmaceutically acceptable salt thereof having a group derived from a steroidal or non-steroidal anti-inflammatory compound, wherein the method is applied to a human joint disease patient having a BMI of at least 25 $kg/m^2$.

[4] The use of a modified hyaluronic acid or a pharmaceutically acceptable salt thereof having a group derived from a steroidal or non-steroidal anti-inflammatory compound in the manufacture of a composition for treating joint disease, wherein the composition is for treating joint disease in a human joint disease patient having a BMI of at least 25 kg/m$^2$.

[5] A method for treating human joint disease, including a step of administering a composition containing a modified hyaluronic acid or a pharmaceutically acceptable salt thereof having a group derived from a steroidal or non-steroidal anti-inflammatory compound to a joint of a patient, wherein the patient is a joint disease patient having a BMI of at least 25 kg/m$^2$.

DESCRIPTION OF EMBODIMENTS

Embodiments of the present invention are explained below with examples.

One aspect of the present invention relates to a composition for treating joint disease, containing a modified hyaluronic acid or a pharmaceutically acceptable salt thereof having a group derived from a steroidal or. non-steroidal anti-inflammatory compound, for treating human joint disease patient with a BMI of at least 25 kg/m$^2$.

Another aspect of the present invention relates to a method for treating joint disease, including the administration of an effective dose of a modified hyaluronic acid or a pharmaceutically acceptable salt thereof having a group derived from a steroidal or non-steroidal anti-inflammatory compound to a human joint disease patient having a BMI of at least 25 kg/m$^2$.

Another aspect of the present invention relates to a composition for use in a method for treating a human joint disease patient, wherein the composition contains a modified hyaluronic acid or a pharmaceutically acceptable salt thereof having a group derived from a steroidal or non-steroidal anti-inflammatory compound, and the joint disease patient has a BMI of at least 25 kg/m$^2$.

Yet another aspect of the present invention relates to the use of a modified hyaluronic acid or a pharmaceutically acceptable salt thereof having a group derived from a steroidal or non-steroidal anti-inflammatory compound in the manufacture of composition for treating a human joint disease patient, wherein the joint disease patient has a BMI of at least 25 kg/m$^2$.

With the present invention, particular improvement in medicinal effects can be achieved in a particular patient group among the human joint disease patients by using a composition for treating joint disease containing a modified hyaluronic acid or a pharmaceutically acceptable salt thereof having a group derived from an anti-inflammatory compound. More particularly, excellent improvement effects can be achieved with the composition for treating joint disease in a group of joint disease patients with BMIs of at least 25 kg/m$^2$. The present invention provides a method for treating human joint disease patients that is more effective than conventional treatment methods, as well as a composition and kit and the like for use in this treatment method.

As should, be obvious to those skilled in the art, preferred properties and features of one aspect of the present invention can be applied to other aspects of the invention.

In this Description, a "hyaluronic acid or a pharmaceutically acceptable salt thereof" may be called simply a "hyaluronic acid molecule". Similarly, a "hyaluronic acid or a pharmaceutically acceptable salt, thereof having a group derived from a steroidal or non-steroidal anti-inflammatory compound " may be called simply a "modified hyaluronic acid molecule".

In this Description, examples of "pharmaceutically acceptable salts" include, but are not limited to, metal, salts such as sodium, potassium, calcium, magnesium and barium salts; ammonium salts; amine salts such as methylamine, diethylamine, ethylenediamine, cyclohexylamine and ethanolamine salts; inorganic acid salts such as hydrochlorate, sulfate, hydrogen sulfate, nitrate, phosphate, hydrobromide and hydroiodide salts; and organic acid salts such as acetate, phthalate, fumarate, maleate, oxalate, succinate, methanesulfonate, p-toluenesulfonate, tartrate, bitartrate and malate salts and the like.

In this Description, a "joint disease" is a disease of a joint such as a knee joint, shoulder joint, neck joint, hip joint, spinal joint, temporomandibular joint, finger joint, elbow joint, wrist joint, ankle joint or the like. More specific examples of joint diseases include osteoarthritis, rheumatoid arthritis, articular cartilage injury, osteonecrosis of the knee, femoral necrosis, shoulder arthritis, bacterial arthritis, viral arthritis, neuropathic joint disease and the like. The composition for treating joint disease of the invention is preferably used for osteoarthritis or rheumatoid arthritis, and more preferably for osteoarthritis. Furthermore the composition for treating joint disease of the invention is preferably used to treat joint disease of the knee joint. More preferably, the composition for treating joint disease of the invention is used for osteoarthritis of the knee.

In this Description, "treating" ("treat", "treatment") may refer either to treatment for the disease itself (for example, treatment to cure or ameliorate organic lesions of a disease), or treatment for various symptoms (for example, lowered ADL due to joint problems such as pain, stiffness and joint function, which may be evaluated, for example, based on difficulty in activities of daily living represented by ability to climb stairs or getting in or out of an automobile). Furthermore, treatment includes not only complete cures, but also improvement in some or all symptoms of the disease, as well as prevention and suppression of disease progression (including maintenance and reducing the speed of disease progression). Prevention here includes for example preventing the occurrence of symptoms of joint disease such as joint dysfunction, pain and/or stiffness when such symptoms are not present even though organic lesions are found in the joints. In cases in which no organic lesions are found but symptoms of joint disease such as joint dysfunction, pain and/or stiffness are present, prevention also includes preventing the occurrence of such organic lesions or suppressing the development of those symptoms that are not yet apparent. The composition for treating joint disease of the invention is preferably used to improve, cure, or suppress the progress of symptoms of joint disease, and more preferably to improve or cure such symptoms. In one embodiment, it can be used favorably to improve, cure or suppress the progress of joint pain, or to improve joint function.

In this Description, an "effective dose" means an amount of a component consistent with a rational risk/benefit analysis, and sufficient to obtain the desired response without excessive harmful side-effects (such as toxicity, irritation or allergic response). This "effective dose" may vary depending on such factors as the symptoms, body type, age, sex and the like of the patient receiving administration. However, a person skilled in the art does not require individual, testing for each individual combination, of these factors, and the effective dose in other cases can be determined based on common technical knowledge and the results of one or more test examples (for example, the examples described below).

The hyaluronic acid molecule may be a glycosaminoglycan having a base skeleton composed of N-acetyl-D-glucosamine (1,3)-β linked to D-glucuronic acid to form disaccharide units (constituent disaccharide units) that are linked to each other by repeated (1,4)-β bonds, and is not particularly limited as to structure as long as it is a glycosaminoglycan having such a basic skeleton. Moreover, the hyaluronic acid molecule may be obtained by any method, such as a purified product of animal or microbial origin or a chemically synthesized product or the like, and one obtained by any of these methods may be used. The hyaluronic acid molecule in this Description may also have a network structure including units of the basic skeleton attached to each other via crosslinking groups. Examples of hyaluronic acid molecules having such network structures include the compounds described in WO 2008-063348 and WO 2011-013902. A person skilled in the art can obtain or prepare these compounds appropriately according to the descriptions of these publications and technical common knowledge in the field. Moreover, the entire contents of these publications are incorporated by reference in this Description. In one embodiment, the hyaluronic acid molecule may be one that does not have a network structure introduced between units of the basic skeleton by a crosslinking reaction. Moreover, the hyaluronic acid molecule may also be a derivatized molecule having a reducing end or one in which some of the hydroxyl groups in the molecule have been acetylated, as long as this does not detract from the objects and effects of the present invention.

The weight-average molecular weight of the hyaluronic acid molecule or modified hyaluronic acid molecule is not particularly limited, but may be not less than 10,000 and not more than 5,000,000, or preferably not less than 500,000 and not more than 3,000,000, or more preferably not less than 600,000 and not more than 3,000,000, or yet more preferably not less than 600,000 and not more than 1,200,000. In this Description, the "weight-average molecular weight" is a value measured by the intrinsic viscosity method.

Although the hyaluronic acid molecule and modified hyaluronic acid molecule used in the invention need not be in the form of salts, they may be in the form of pharmaceutically acceptable salts. Examples of pharmaceutically acceptable salts of the hyaluronic acid molecule and modified hyaluronic acid molecule include metal salts such as sodium salts, potassium salts, magnesium salts and calcium salts, and ammonium salts and the like. From the standpoint of greater affinity with living organisms, the hyaluronic acid salt and modified hyaluronic acid salt used are preferably pharmaceutically acceptable alkali metal salts (such as sodium or potassium salts), and sodium salts are especially desirable.

The modified hyaluronic acid molecule can be obtained by bonding an anti-inflammatory compound to a hyaluronic acid molecule with or without an intervening spacer. The modified hyaluronic acid molecule may have one kind of anti-inflammatory compound or two or more anti-inflammatory compounds bonded thereto.

The mode of bonding between the hyaluronic acid molecule and the anti-inflammatory compound is not particularly limited as long as it does not detract from the desired treatment effects for joint disease in this case, and may be covalent bonding for example. For example, the hyaluronic acid molecule and anti-inflammatory compound may be bonded directly by a bonding mode involving amide bond, ether bonds or the like. When the hyaluronic acid molecule and anti-inflammatory compound are bonded via an intervening spacer, the mode of bonding between the hyaluronic molecule and the spacer may be by amide bond, ether bond, ester bond, thioester bond or sulfide bond for example, while the mode of bonding between the spacer and the anti-inflammatory compound may be by amide bond, ether bond, ester bond, thioester bond or sulfide bond for example.

In a preferred embodiment, the anti-inflammatory compound is bonded to the hyaluronic acid molecule via a spacer in the modified hyaluronic acid molecule. By selecting a functional group for the spacer that matches a functional group of the anti-inflammatory compound, it is possible to introduce the anti-inflammatory compound into the hyaluronic acid molecule by the desired bonding mode.

From the standpoint of biodegradability, a preferred embodiment provides a modified hyaluronic acid molecule in which a group derived from the anti-inflammatory compound is covalently bonded to a hyaluronic acid skeleton via a spacer represented by Formula (1) below. In this Description, a "hyaluronic acid skeleton" is the structural part of the modified hyaluronic acid molecule that derives from a hyaluronic acid molecule.

[C1]

$$-NR^1-R^2-O-  \quad (1)$$

In Formula (1), $R^1$ is a hydrogen atom or alkyl group having carbon number of not less than 1 and not more than 3; and $R^2$ is an optionally substituted linear alkylene group having carbon number of not less than 1 and not more than 12. $R^1$ is preferably a hydrogen atom. $R^2$ is preferably an optionally substituted linear alkylene group having carbon number of not less than 1 and not more than 4, and more preferably an unsubstituted linear alkylene group having carbon number of not less than 1 and not more than 2. For purposes of sustaining the medicinal effects, $R^2$ is still more preferably an ethylene group, and it is especially desirable for $R^1$ to be a hydrogen atom and $R^2$ an ethylene group.

Examples of substituents of $R^2$ include aryl groups having carbon number of not less than 6 and not more than 20, alkoxy groups having carbon number of not less than 1 and not more than 11, acyl groups having carbon number of not less than 1 and not more than 11, carboxyl groups, and halogen atoms (such as fluorine, chlorine, bromine and iodine atoms) and the like.

From the standpoint of biodegradability, a more preferred embodiment provides a modified hyaluronic acid molecule containing a constituent disaccharide unit represented by Formula (2) below.

[C2]

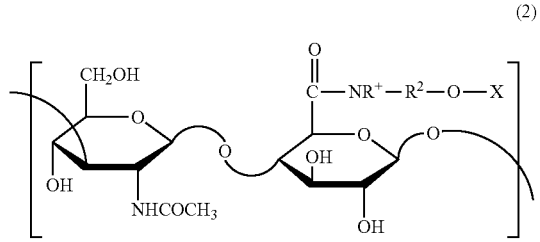

(2)

$R^1$ and $R^2$ in Formula (2) are defined as in Formula (1), and the definitions of Formula (1) may be applied appropriately. In Formula (2), X represents a group derived from an anti-inflammatory compound.

To achieve a balance between the effective concentration of the anti-inflammatory compound and the solubility in an aqueous composition, a preferred embodiment provides a modified hyaluronic acid molecule in which the proportion of constituent units represented by Formula (2) (corresponding to the introduction rate described below) as a percentage of the total constituent disaccharide units making up the modified hyaluronic acid is not less than 0.1 mol % and not more than 80 mol %. The proportion of constituent units represented by Formula (2) as a percentage to the total constituent disaccharide units constituting the modified hyaluronic acid is more preferably not less than 5 mol % and not more than 50 mol %, or still more preferably not less than 10 mol % and not more than 30 mol %, or yet more preferably not less than 15 mol % and not more than 30 mol %. The proportion of constituent units represented by Formula (2) can be adjusted by varying the condensing agent, condensing aid, reaction equivalent of the spacer molecule and reaction equivalent of the anti-inflammatory compound and the like in the reaction step that introduces the anti-inflammatory compound into the hyaluronic acid molecule. Of the constituent disaccharide units in the modified hyaluronic acid molecule, a glucuronic acid derived unit in a constituent disaccharide unit other than the constituent disaccharide unit represented by Formula (2) above may have either a carboxyl group or a carboxylic acid salt group, but preferably has an alkali metal salt (for example sodium or potassium salt) group.

For the compound used as a spacer (spacer compound), a compound having at least one functional group that binds to the hyaluronic acid molecule and at least one functional group that, binds to the anti-inflammatory compound may be selected appropriately according to the mode of bonding between the hyaluronic acid molecule and the anti-inflammatory compound.

For example, when introducing a spacer by forming an amide bond with a carboxyl group of the hyaluronic acid molecule, a spacer compound having an amino group may be selected. When introducing a spacer by forming an ester bond with a carboxyl group of the hyaluronic molecule, a spacer compound having a hydroxyl group may be selected. When introducing a spacer by forming an ester bond with a hydroxyl group of the hyaluronic acid molecule, a spacer compound having a carboxyl group may be selected. For the standpoint of ease of introduction into the hyaluronic acid molecule and stability in vivo, a preferred embodiment is a spacer compound having an amino group.

Similarly, when introducing a spacer by forming an ester bond with a carboxyl group of the anti-inflammatory compound, a spacer compound having a hydroxyl group may be selected. When introducing a spacer by forming an amide bond with a carboxyl group of the anti-inflammatory compound, a spacer compound having an amino group may be selected. When introducing a spacer by forming an ester bond with a hydroxyl group of the anti-inflammatory compound, a spacer compound having a carboxyl group may be selected. When introducing a spacer by forming a thioester bond with a mercapto group of the anti-inflammatory compound, a spacer compound having a carboxyl group may be selected. From the standpoint of release of the anti-inflammatory compound by biodegradation, the mode of bonding between the spacer and the anti-inflammatory compound is preferably ester bonding or thioester bonding, and more preferably ester bonding.

As discussed above, the spacer compound may be selected appropriately according to the functional groups of the hyaluronic acid molecule and anti-inflammatory compound, and examples include diaminoalkanes having carbon number of not less than 2 and not more than 18, optionally substituted aminoalkyl alcohols having carbon number of not less than 2 and not more than 12, and amino acids and the like. An amino acid may be a natural or non-natural amino acid, without any particular limitations, and examples include glycine, β-alanine and γ-aminobutyric acid.

Using a spacer compound (polyvalent spacer compound) having multiple functional groups capable of forming bonds with anti-inflammatory compounds, it is possible to bond multiple anti-inflammatory compounds to a single spacer. It is thus possible to introduce multiple anti-inflammatory compounds into a single functional group (such as a single carboxyl group) of a hyaluronic acid molecule. When using a polyvalent spacer compound, it is also possible to introduce more anti-inflammatory compounds by reacting only some of the hydrophilic groups such as carboxyl groups and hydroxyl groups of the hyaluronic acid molecule with the polyvalent spacer compound. This means that a polyvalent spacer compound is advantageous from the standpoint of water solubility when the composition for treating joint disease is made into an aqueous composition. Examples of such polyvalent spacer compounds include 2-aminopropane-1,3-diol, serine, threonine, 2-amino-1,5-pentanediol, 3-amino-1,2-propanediol, tris(hydroxymethyl)aminomethane, and derivatives of these and the like.

As the method for introducing the spacer and anti-inflammatory compound into the hyaluronic acid molecule, the anti-inflammatory compound may be introduced into a hyaluronic acid molecule having an introduced spacer, or the hyaluronic acid molecule may be reacted with an anti-inflammatory compound having an introduced spacer.

The methods of bonding the anti-inflammatory compound, hyaluronic acid molecule and spacer compound are not particularly limited. For example, any method commonly used in such bonding reactions may be used as long as it is a method capable of forming ester bond, amide bond and thioester bond and the like, and the reaction conditions can be determined and selected appropriately by a person skilled in the art.

The bonding reaction between the hyaluronic acid molecule and the spacer compound or spacer-bonded anti-inflammatory compound can be achieved using either a carboxyl group or a hydroxyl group of the hyaluronic acid molecule, but can be more easily achieved using the carboxyl group due to the greater reactivity of the functional group. Methods for achieving such bonding include for example methods using water-soluble condensing agents such as water-soluble carbodiimides (for example, 1-ethyl-3-(3-dimethylaminopropyl)-carbodiimide hydrochloride (EDCI·HCl) or 1-ethyl-3-(3-dimethylaminopropyl) carbodiimide methionodide), methods using these condensing agents together with condensing aids such as N-hydroxysuccinimide (HOSu) and N-hydrozybenzotriazole (HOBt), and active ester methods, acid anhydride methods and the like. Bonding between the hyaluronic acid molecule and the spacer compound or spacer-bound anti-inflammatory compound is preferably ester bond or amide bond, and more preferably amide bond.

The introduction rate of the anti-inflammatory compound in the modified hyaluronic acid molecule (in this Description, the "introduction rate of the anti-inflammatory compound in the modified hyaluronic acid molecule" is sometimes called simply the "introduction rate") is preferably not less than 0.1 mol % and not more than 80 mol %, or more preferably not less than 5 mol % and not more than 50 mol %, or still more preferably not less than 10 mol % and not more than 30 mol %, or especially not less than 15 mol % and not more than 30 mol % in order to achieve a balance between the effective concentration of the anti-inflammatory compound and the solubility in an aqueous composition.

The "introduction rate" in this Description is a value calculated by Calculation Formula 1 below, and can be determined by absorbance measurement for example. More specifically, it can be obtained by entering the number of moles of constituent disaccharide units of the modified hyaluronic acid molecule as calculated by the carbazole absorbance method and the number of moles of the anti-inflammatory compound as calculated from a calibration curve prepared in advance based on the characteristic absorbance values of each anti-inflammatory compound into the following Calculation Formula 1. The introduction rate can be adjusted by varying the condensing agent, condensing aid, reaction equivalent of the spacer molecule and reaction equivalent of the anti-inflammatory compound and the like in the reaction step of introducing the anti-inflammatory compound into the hyaluronic acid molecule.

[Math. 1]
Calculation Formula 1;

Introduction rate (mol %)=(Number of groups derived from anti-inflammatory compound/number of constituent disaccharide units)×100

In one embodiment, alkali treatment is performed after the reaction that introduces the anti-inflammatory compound into the hyaluronic acid molecule via the spacer. The fluidity of a composition containing the modified hyaluronic acid molecule and the solubility of the modified hyaluronic acid molecule in an aqueous solvent can sometimes be improved in this way. This alkali treatment is not particularly limited as long as it is treatment to make the reaction solution more alkaline after the introduction reaction. A specific example is a method of adding either an organic base or an inorganic base to the solution, and considering subsequent treatment and the like it is preferably to add an inorganic base. In particular, a weak base such as sodium hydrogen carbonate or sodium carbonate is desirable because it is less likely to affect the hyaluronic acid molecule and anti-inflammatory compound. The pH conditions of this alkali treatment may be not less than 7.2 and not more than 11, or preferably not less than 7.5 and not more than 10 for example. The treatment time for alkali treatment is also not particularly limited, but may be not less than 2 hours and not more than 12 hours for example, or preferably not less than 2 and not more than 6 hours. As a specific example, an anti-inflammatory compound derivative with an introduced spacer can be first reacted with a hyaluronic acid molecule, after which a weak alkali such as sodium hydrogen carbonate is added to the reaction solution and stirred for several hours to treat the solution, which is then neutralized and post-treated by ethanol sedimentation, drying and the like to obtain the target modified hyaluronic acid molecule.

A conventional known steroidal compound or non-steroidal compound having anti-inflammatory action may be used as the "anti-inflammatory compound" in the present Description, Specific examples of steroidal anti-inflammatory compounds include hydrocortisone, cortisone acetate ester, dexamethasone, dexamethasone pal/nitate ester, betamethasone, triamcinolone, triamcinolone acetonide, prednisolone, methyl prednisolone, paramethasone acetate ester, halopredone acetate, prednisolone farnesylate, tetracosactide acetate and the like.

In this Description, examples of non-steroidal anti-inflammatory compounds (hereunder also called "NSAIDs" in the Description) include arylacetic acid compounds (such as indomethacin, sulindac, tolmetin, diclofenac, etodoiac, acemetacin, proglumetacin, amfenac, felbinac, nabumetone, rnofezolac, alclofenac and pharmaceutically acceptable salts of these compounds and the like), oxicam compounds (such as piroxicam, lornoxicam, raeloxicam, ampiroxicam, tenoxicam and pharmaceutically acceptable salts of these compounds and the like), propionic acid compounds (such as ibuprofen, naproxen, ketoprofen, fenoprofen, flurbiprofen, tiaprofenic acid, oxaprozin, zaltoprofen, loxoprofen, fenbufen, aluminoprofen, pranoprofen, and pharmaceutically acceptable salts of these compounds and the like), fenamic acid compounds (such as mefenamic acid, flufenamic acid, meclofenamic acid, tolfenamic acid, floctafenine, and pharmaceutically acceptable salts of these compounds and the like), coxib compounds (such as celecoxib and the like), salicylic acid compounds (such as aspirin, salicylic acid, salsaiate, diflunisal, and pharmaceutically acceptable salts of these compounds and the like), acetaminophen, tiaramide, epirizole, emorfazone, tinoridine, tolmetin, diflunisal floctafenine, disease-modifying anti-rheumatic drugs (DMARDs) (such as actarit, salazosulfapyridine, bucillamine, lefiunomide, penicillamine, auranofin, mizoribine, lobenzarit, tacrolimus, methotrexate, infliximab, etanercept, adalimumab, golimumab, certolizumab and tocilizurnab) and the like.

To facilitate introduction of the anti-inflammatory compound into the hyaluronic acid molecule, a compound having a carboxyl group or carboxylic acid salt group in the side chain, such as indomethacin, sulindac, tolmetin, diclofenac, etodolac, acematacin, amfenac, felbinac, mofezolac, alclofenac, ibuprofen, naproxen, ketoprofen, fenoprofen, flurbiprofen, tiaprofenic acid, oxaprozin, zaltoprofen, loxoprofen, fenbufen, aluminoprofen, pranoprofen, mefenamic acid, flufenamic acid, meclofenamic acid, tolfenamic acid, aspirin, salicylic acid, salsaiate, diflunisal, actarit, salazosulfapyridine, bucillamine or a pharmaceutically acceptable salt of these compounds, is preferred out of the anti-inflammatory compounds given as examples above.

From the standpoint of its pharmacological effects, the anti-inflammatory compound is preferably an arylacetic acid compound such as those given as examples above, and diclofenac or its pharmaceutically acceptable salt is more preferred.

In a preferred embodiment, a compound having the molecular skeleton represented by Formula (3) below is used as the anti-inflammatory compound.

[C3]

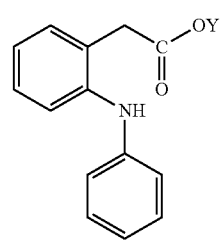

(3)

In Formula (3), Y is a hydrogen atom, sodium atom or potassium atom.

In a more preferred embodiment, a compound represented by Formula (3') below is used as the anti-inflammatory compound.

[C4]

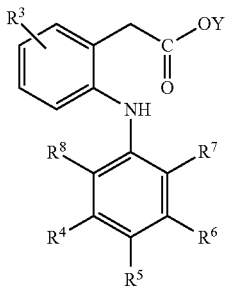

(3')

In Formula (3'), $R^3$ is selected from a group consisting of the straight or branched chain alkyl groups having carbon number of not less than 1 and not more than 6, straight or branched chain alkoxy groups having carbon number of not less than 1 and not more than 6 and a hydrogen atom. In one embodiment, $R^3$ is attached at the 5-position when a carboxymethyl group is at position 1 and —NH- is at position 2 on the benzene ring to which $R^3$ is attached. $R^4$, $R^5$ and $R^6$ are each independently selected from a group consisting of the straight or branched chain alkyl groups having carbon number of not less than 1 and not more than 6, straight or branched chain alkoxy groups having carbon number of not less than 1 and not more than 6, a hydroxyl group, the halogen atoms (for example, fluorine, chlorine, bromine and iodine atoms) and a hydrogen atom. $R^7$ and $R^8$ are each independently selected from a group consisting of the straight or branched chain alkyl groups having carbon number of not less than 1 and not more than 6, straight or branched chain alkoxy groups having carbon number of not less than 1 and not more than 6, a trifluoromethyl group, and the halogen atoms. However, at least, one of $R^7$ and $R^8$ is a halogen atom. In Formula (3'), Y is defined as in Formula (3). A more preferred example of the anti-inflammatory compound above is diclofenac, in which $R^3$, $R^4$, $R^5$ and $R^6$ are hydrogen atoms, $R^7$ and $R^8$ are chlorine atoms, and Y is a hydrogen atom.

An example of the compound represented by Formula (3') above is a compound described in WO 99/11605. The content described in this publication is incorporated by reference in this Description.

In one embodiment, the composition for treating joint disease of the present invention contains the modified hyaluronic acid molecule in the amount of not less than 0.01 wt % and not more than 80 wt % of the composition. In another embodiment, the composition for treating joint disease of the present invention contains the modified hyaluronic acid molecule in the amount of not less than 0.1 wt % and not more than 10 wt %.

The composition for treating joint disease of the invention may contain a pharmaceutically acceptable carrier in addition to the modified hyaluronic acid mentioned above. Preferred examples of this pharmaceutically acceptable carrier include aqueous solvents such as water for injection, phosphate-buffered saltine (PBS), physiological saline and Ringer's solution. In one embodiment, the composition for treating joint disease is prepared by mixing this physiologically acceptable carrier with the modified hyaluronic acid molecule. Additives such as buffers may also be added to the composition as necessary. Moreover, the composition for treating joint disease may also be treated by dust removal, disinfection, sterilization or the like with a filter or the like after the components are mixed.

In one embodiment, the composition for treating joint disease of the invention is used by administration into a joint at a frequency of once per period of 4 weeks or more. From the standpoint of the medicinal effects, the composition for treating joint disease of the invention is preferably administered once per period of not less than 4 weeks and not more than 52 weeks, or more preferably once per period of not less than 4 weeks and not more than 12 weeks, or still more preferably once per period of not less than 4 weeks and not more than 3 weeks, or most preferably once in a period of four weeks to less than eight weeks.

In one embodiment, the composition for treating joint disease of the invention is administered to a joint at a frequency of once about every four weeks.

The number of administrations of the composition for treating joint disease of the invention is determined appropriately according to the condition of the patient's joint disease, but may be at least one, or preferably at least two, or more preferably at least three administrations.

In a preferred embodiment, the treatment period with the composition for treating joint disease of the invention extends from the start of administration until the patient no longer has subjective symptoms, and the number of administrations during this treatment period is at least one. In a more preferred embodiment, the number of administrations of the composition for treating joint disease is not less than 2 and not more than 13, or more preferably not less than 3 and not more than 10. "Subjective symptoms" here mean for example subjective symptoms associated with pain or physical function (joint function). Subjective symptoms can be evaluated for example using the WOMAC® A and C described in the examples.

In a case of multiple dose administration, individual dosing interval of the composition for treating joint disease of the present invention may be the same or different. However, the joint disease treatment process may include a dosing interval of less than four weeks. Preferably, each dosing interval is four weeks or more. In a preferred embodiment, the composition for treating joint disease of the present invention is administered at predetermined intervals of four weeks or more.

In one embodiment, from the perspective of medicinal effect, preferably not less than 5 mg and not more than 100 mg, or more preferably not less than 10 mg and not more than 50 mg, or still more preferably not less than 20 mg and not more than 40 mg, or most preferably about 30 mg of the modified hyaluronic acid molecule is administered in one administration. One aspect of the invention provides a composition for treating joint disease that is used for such administration.

In one embodiment, from the perspective of medicinal effect, a composition for treating joint disease containing the anti-inflammatory compound in the amount of preferably not less than 0.1 mg and not more than 20 mg, or more preferably not less than 0.5 mg and not more than 10 mg, or still more preferably more than not less than 1 mg and not more than 5 mg is administered per administration. One aspect of the present invention provides a composition for treating joint disease that is used for such administration.

When the composition for treating joint disease of the present invention is an aqueous composition containing an aqueous solvent such as those given as examples above, preferably not less than 0.5 ml and not more than 10 ml, or more preferably not less than 2 mL and not more than 4 mL of the aqueous composition is administered per administration from the standpoint of convenience of treatment.

In a preferred embodiment, not less than 10 mg and not more than 50 mg of the modified hyaluronic acid molecule per administration is administered at least twice at a frequency of once every four weeks to less than eight weeks. One aspect of the invention provides a composition for treating joint disease that is used for such administration.

In another preferred embodiment, not less than 20 mg and not more than 40 mg of the modified hyaluronic acid molecule per administration is administered at least three times at a frequency of once every four weeks to less than eight weeks. One aspect of the invention provides a composition for treating joint disease that is used for such administration.

The mode of administration of the composition for treating joint disease of the invention is not particularly limited, and examples include intraarticular injection, intravenous injection, intramuscular injection, subcutaneous injection, transdermal injection and the like. The composition for treating joint disease of the invention may be administered by any oral or non-oral administration route, but is preferably administered by intraarticular injection.

The dosage form of the composition for treating joint disease of the invention is not particularly limited, and it may be formulated as an injection, cream, ointment, solid preparation for external use, lotion, spray, gel, patch or any other dosage form according to the administration route. Of these, the dosage form of the composition for treating joint disease of the invention is preferably an injection. In one embodiment, the composition for treating joint disease of the invention is administered into a joint as an injection. These formulations can be manufactured by ordinary methods.

The composition for treating joint disease of the invention is intended for humans (human patients). From the perspective of the medicinal effects, the composition for treating joint disease of the invention is preferably administered to a joint disease patient having pain for at least 12 weeks (that is, the pain duration period is at least 12 weeks). In other words, in one embodiment of the invention the target is a joint disease patient having pain continuously for at least 12 weeks. "A joint disease patient having pain for at least 12 weeks" here means a patient who has had subjective symptoms of pain in the part affected by the joint disease to be treated continuously for 12 weeks or more before the start of administration of the composition for treating joint disease of the invention.

From a similar perspective, the composition for treating joint disease of the invention is more preferably administered to a joint disease patient; having pain for at least 26 weeks (about half a year). That is, one embodiment of the invention is targeted at a joint, disease patient having pain that has persisted for 26 weeks or more. "A joint disease patient having pain for at least 26 weeks" here means a patient who has had subjective symptoms of pain continuously for 26 weeks or more in the part affected by the joint disease to be treated before the start of administration of the composition for treating joint disease of the invention.

Although the joint disease treatment of the invention is not restricted in terms of mechanism, the composition is expected to be especially effective in patients with long pain duration periods due to the synergistic effect of the anti-inflammatory compound and the hyaluronic acid molecule.

The composition for treating joint disease of the invention is administered to a joint disease patient having a BMI (patient weight (kg)/(patient height (m))$^2$) of at least 25 kg/m$^2$. A BMI of at least 25 kg/m$^2$ is a benchmark for obesity according to the 2011 obesity criteria of the Japan Society for the Study of Obesity, and an association with increased occurrence of complications (such as glucose intolerance, lipid abnormalities, high blood pressure, etc.) has been indicated.

As shown in detail in the examples below, dramatic improvement effects from the composition for treating joint disease of the invention have been confirmed in a group of patients with BMIs of at least 25 kg/m$^2$ out of the joint disease patients. Even assuming that the burden on the joints increases (joint disease becomes more likely) as the BMI increases or in other words as obesity progresses, this dramatic improvement effect is unexpected considering that a good response from treatment was obtained with the composition for treating joint disease in a group of patients with BMIs within the specified range. The mechanism for this dramatic improvement is unknown, but it is speculated that the synergistic effect of the anti-inflammatory compound and hyaluronic acid may be particularly effective in joint disease patients in whom the burden on the joints is severe due to obesity. This mechanism is only a speculation, and the joint disease treatment of the invention is not restricted as to the mechanism of action.

More preferably, the composition for treating joint disease of the invention is administered to a joint disease patient having a BMI of less than 35 kg/m$^2$. That is, one embodiment of the invention is targeted at joint disease patients with BMIs of not less than 25 kg/m$^2$ to less than 35 kg/m$^2$. This BMI is a value measured within four weeks of the start of administration of the composition for treating joint disease of the invention, and preferably a value measured within two weeks of the start of administration of the composition for treating joint disease of the invention.

One embodiment provides a syringe containing the composition for treating joint disease of the invention packed in a syringe barrel. One embodiment can also provide a kit containing a syringe containing the composition for treating joint disease of the invention packed in a syringe barrel. This syringe is equipped with a plunger or the like for ejecting the drug, so that the composition for treating joint disease of the invention can be ejected. In one embodiment, the composition for treating joint disease packed in the syringe can be provided in a sterile state. In one embodiment, the syringe barrel is filled in advance with a single dose of the composition for treating joint disease. The kit may also be a kit containing a solution of the modified hyaluronic acid molecule dissolved in phosphate-buffered saline, physiological saline or water for injection and packed in a syringe barrel, together with a medical syringe sealed with a slidable drug ejection plunger. A commonly used plunger may be used as the plunger for drug injection, which is formed from an elastic material such as rubber or synthetic rubber and inserted slidably in tight contact with the syringe. The kit may also contain a plunger rod for pushing down on the plunger to eject the drug, as well, as an instruction manual, package insert or the like.

EMBODIMENTS

Examples of preferred embodiments of the invention are given below.

[1] A composition for treating a human joint disease, wherein the composition comprising a modified hyaluronic acid or a pharmaceutically acceptable salt thereof having a group derived from a steroidal or non-steroidal anti-inflammatory compound, which is administered for the joint disease patient having a BMI of at least 25 kg/m².

[2] The composition according to [1] above, wherein the joint disease patient having a BMI of less than 35 kg/m2.

[3] The composition according to [1] or [2] above, which is administered for the joint disease patient having duration of pain for 26 weeks or more.

[4] The composition according to any one of [1] to [3] above, which is an injection.

[5] The composition according to any one of [1] to [4] above, wherein the group derived from an anti-inflammatory compound is bonded to a hyaluronic acid or a pharmaceutically acceptable salt thereof via a spacer in the modified hyaluronic acid or a pharmaceutically acceptable salt thereof.

[6] The composition according to [3] above, wherein the mode of bonding between the hyaluronic acid or a pharmaceutically acceptable salt thereof and the spacer is selected from the group consisting of amide bond, ether bond, ester bond, thioester bond and sulfide bond. [7] The composition according to [5] or [6] above, herein the mode of bonding between the spacer and the group derived from an anti-inflammatory compound is selected from the group consisting of amide bond, ether bond, ester bond, thioester bond and sulfide bond. [8] The composition according to any one of [1] to [7] above, wherein the group derived from an anti-inflammatory compound is covalently bonded to a hyaluronic acid skeleton via a spacer having a structure of the following Formula (1):

$$-NR^1-R^2-O- \qquad (1)$$

In Formula (1), $R^1$ is a hydrogen atom or an alkyl group having carbon number of 1 to 3; and $R^2$ is an optionally substituted linear alkylene group having carbon number of 1 to 12.

[9] The composition according to [8] above, wherein $R^1$ is a hydrogen atom and $R^2$ is an ethylene group.

[10] The composition according to any one of [1] to [8] above, wherein the modified hyaluronic acid or a pharmaceutically acceptable salt thereof contains a structural unit of the following Formula (2):

[C6]

(2)

in Formula (2), $R^1$ is a hydrogen atom or a alkyl group having carbon number of 1 to 3; $R^2$ is an optionally substituted linear alkylene group having carbon number of 1 to 12; and X is the group derived from an anti-inflammatory compound.

[11] The composition according to [10] above, wherein $R^1$ is a hydrogen atom and $R^2$ is an ethylene group.

[12] The composition according to [10] or [11] above, wherein the percent ratio of the number of structural units of the Formula (2) to the total number of constituent disaccharide units constituting the modified hyaluronic acid or a pharmaceutically acceptable salt thereof is not less than 0.1 mol % and not more than 30 mol %.

[13] The composition according to any one of [1] to [12] above, wherein a dose of not less than 5 mg and more than 100 mg by weight of the modified hyaluronic acid or a pharmaceutically acceptable salt thereof is used in a single administration.

[14] The composition according to any one of [1] to [13] above, wherein a dose of not less than 0.1 mg and not more than 20 mg by weight of the anti-inflammatory compound is administered in a single administration.

[15] The composition according to any one of [1] to [14] above, wherein the joint disease is osteoarthritis.

[16] The composition according to any one of [1] to [15] above, wherein the treatment consists in improving, curing or suppressing the progress of symptoms.

[17] The composition according to [16] above, wherein the treatment consists in improving, curing or suppressing the progress of joint pain, or Improving joint function.

[18] The composition according to any one of [1] to [17] above, further containing a pharmaceutically acceptable carrier.

[19] The composition according to any one of [1] to [18] above, wherein the steroidal or non-steroidal anti-inflammatory compound is diclofenac or a pharmaceutically acceptable salt thereof.

[20] The composition according to any one of [1] to [19] above, wherein the group derived from a steroidal or non-steroidal anti-inflammatory compound is bonded to hyaluronic acid or a pharmaceutically acceptable salt thereof having a weight-average molecular weight of not less than 10,000 and not more than 5,000,000 in the modified hyaluronic acid or a pharmaceutically acceptable salt thereof.

[21] A kit containing a syringe comprising the composition according to any one of [1] to [20] packed in a syringe barrel.

[22] A composition for use in a method for treating joint disease of human joint, disease patients, containing a modified hyaluronic acid or a pharmaceutically acceptable salt thereof having a group derived from a steroidal or non-steroidal anti-inflammatory compound, wherein the method is applied to a human joint disease patient having a BMI of at least 25 kg/m².

[23] The composition according to [22] above, wherein the joint disease patient to which the method is applied having a BMI of less than 35 kg/m².

[24] The composition according to [22] or [23] above, wherein the method is applied to a human joint disease patient having duration of pain for 26 weeks or more.

[25] The composition according to any one of [22] to [24] above, wherein the method is performed by injection.

[26] The composition according to any one of [22] to [25] above, wherein the modified hyaluronic acid or a pharmaceutically acceptable salt thereof includes the group derived from an anti-inflammatory compound bonded to hyaluronic acid or a pharmaceutically acceptable salt thereof via a spacer.

[27] The composition according to [26] above, wherein the mode of bonding between the hyaluronic acid or a pharmaceutically acceptable salt thereof and the spacer is selected from the group consisting of amide bond, ether bond, ester bond, thioester bond and sulfide bond.

[28] The composition according to [26] or [27] above, wherein the mode of bonding between the spacer and the group derived from an anti-inflammatory compound is selected from the group consisting of amide bond, ether bond, ester bond, thioester bond and sulfide bond.

[25] The composition according to any one of [22] to [28] above, wherein the group derived from an anti-inflammatory compound is covalently bonded to the hyaluronic acid skeleton via a spacer having a structure of the following Formula (1):

[C7]

$$-NR^1-R^2-O- \quad (1)$$

in Formula (1), $R^1$ is a hydrogen atom or a alkyl group having carbon number of 1 to 3; and $R^2$ is an optionally substituted linear alkylene group having carbon number of 1 to 12.

[30] The composition according to [29] above, wherein $R^1$ is a hydrogen atom and $R^2$ is an ethylene group.

[31] The composition according to any one of [22] to [29], wherein the modified hyaluronic acid or a pharmaceutically acceptable salt thereof contains a structural unit of the following Formula (2):

[C8]

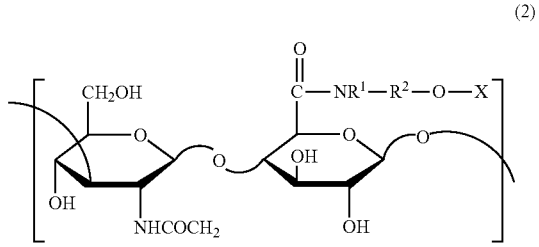

(2)

in Formula (2), $R^1$ is a hydrogen atom or a alkyl group having carbon number of 1 to 3; $R^2$ is an optionally substituted linear alkylene group having carbon number of 1 to 12; and X is a group derived from an anti-inflammatory compound.

[32] The composition according to [31] above, wherein $R^1$ is a hydrogen atom and $R^2$ is an ethylene group.

[33] The composition according to [31] or [32] above, wherein the percent ratio of the number of structural units of the Formula (2) to the total number of constituent disaccharide units constituting the modified hyaluronic acid or a pharmaceutically acceptable salt thereof is not less than 0.1 mol % and not more than 30 mol %.

[34] The composition according to any one of [22] to [33] above, wherein the method includes administering a dose of not less than 5 mg and not more than 100 mg by weight of the modified hyaluronic acid or a pharmaceutically acceptable salt thereof in a single administration.

[35] The composition according to any one of [22] to [34] above, wherein the method includes administering a dose of not less than 0.1 mg and not more than 20 mg by weight of the anti-inflammatory compound in a single administration.

[36] The composition according to any one of [22] to [35] above, wherein the joint disease is osteoarthritis.

[37] The composition according to any one of [22] to [36] above, wherein the treatment consists in improving, curing or suppressing the progress of symptoms.

[38] The composition according to [37] above, wherein the treatment consists in improving, curing or suppressing the progress of joint pain, or improving joint function.

[39] The composition according to any one of [22] to [38] above, further containing a pharmaceutically acceptable carrier.

[40] The composition according to any of [22] to [39] above, wherein the steroidal or non-steroidal anti-inflammatory compound is diclofenac or a pharmaceutically acceptable salt thereof.

[41] The composition according to any one of [22] to [40] above, wherein the group derived from a steroidal or non-steroidal anti-inflammatory compound is bonded to hyaluronic acid or a pharmaceutically acceptable salt thereof having a weight-average molecular weight of 10,000 to 5,000,000 in the modified hyaluronic acid or a pharmaceutically acceptable salt thereof.

[42] The use of a modified hyaluronic acid or a pharmaceutically acceptable salt thereof having a group derived from a steroidal or non-steroidal anti-inflammatory compound in the manufacture of a composition for treating joint disease, wherein the composition is for treating joint disease in a human joint disease patient with a BMI of at least 25 kg/m$^2$.

[43] The use according to [42] above, wherein the composition is for treating joint disease in a human joint disease patient with a BMI of less than 35 kg/m$^2$.

[4] A method for treating human joint, disease, including a step of administering a composition containing a modified hyaluronic acid or a pharmaceutically acceptable salt thereof having a group derived from a steroidal or non-steroidal anti-inflammatory compound to a joint of a patient, wherein the patient is a joint disease patient having a BMI of at least 25 kg/m$^2$.

[45] The method according to [44] above, wherein the patient having a BMI of leas than 35 kg/m$^2$.

[46] The method according to [44] or [45] above, wherein the administration is performed by injection.

EXAMPLES

Preferred embodiments of the invention are explained in detail below with reference to examples, but the scope of the present invention is in no way limited to these examples.

Unless otherwise specified, operations and measurements of physical properties and the like were performed under conditions of room temperature (not less than 20° C. and not more than 25° C.), not less than 40% and not more than 50% RH.

Synthesis Examples

Sodium hyaluronate with introduced aminoethanol-diclofenac (test substance) was synthesized by the methods described in the examples of WO 2005/066214 (weight average molecular weight of hyaluronic acid: 300,000, introduction rate: 18 mol %).

More specifically, this was synthesized by the following procedures.

2.155 g (10.5 mmol) of 2-bromoethylamine hydrobromide was dissolved, in 20 mL of dichl or cinethane, 1.463 ml, (10.5 mmol) of triethylamine was added under ice cooling, and 5 mL of a dichloromethane solution of 2.299 g (10.5 mmol) of di-tert-butyl-dicarbonate (Boc$_2$O) was further added and stirred in. This was stirred for 90 minutes at room temperature, ethyl acetate was added, and the mixture was separately washed successively with 5 wt % aqueous citric acid solution, water, and saturated saline. After dehydration with sodium sulfate, the solvent was distilled off under reduced pressure to obtain Boc-aminoethyl bromide.

5 mL of a dimethylformamide (DMF) solution of 2.237 g (10.2 mmol) of the Boc-aminoethyl bromide obtained above was ice cooled, 6 mL of a DMF solution of 3.255 g (10.2 mmol) of diclofenac sodium was added, and the mixture was stirred overnight at room temperature. This was stirred for 11 hours at 60° C., and then stirred overnight at room temperature. Ethyl acetate was added, and the mixture was separately washed successively with 5 wt % sodium hydrogen carbonate aqueous solution, water, and saturated saline. After dehydration with sodium sulfate, the ethyl acetate was distilled off under reduced pressure. The residue was purified by silica gel column chromatography (toluene:ethyl acetate=20:1 (v/v), 0.5 vol % triethylamine) to obtain Boc-aminoethanol-diclofenac.

2.108 g (4.80 mmol) of the Boc-aminoethanol-diclofenac obtained above was dissolved in 5 mL of dichloromethane, 20 mL of 4 M hydrochloric acid/ethyl acetate was added under ice cooling, and the mixture was stirred for 2.5 hours. This was precipitated by addition of diethyl ether and hexane, and the precipitate was vacuum dried. Aminoethanol-diclofenac hydrochloride was obtained in this way, and the structure was identified by 1H-NMR:

$^1$H-NMR (500 MHz, CDCl$_3$) δ (ppm)=3.18 (2H, t, NH$_2$CH$_2$CH$_2$O-), 3.94 (2H, s, Ph—CH$_2$—CO), 4.37 (2H, t, NH$_2$CH$_2$CH$_2$O-), 6.47-7.31 (8H, m, Aromatic H, NH).

500 mg (1.25 mmol/disaccharide units) of hyaluronic acid with a weight-average molecular weight of 800,000 was dissolved in 56.3 mL water/56.3 mL dioxane, 0.5 mL of hydroxysuccinimide (1 mmol)/water, 0.5 mL of water-soluble carbodiimide hydrochloride (WSCI·HCl) (0.5 mmol)/water, and the aminoethanol-diclofenac hydrochloride (0.5 mmol)/(water:dioxane=1:1 (v/v), 5 mL) obtained above were added, and the mixture was stirred during a whole day and night. 7.5 mL of a 5 wt % sodium hydrogen carbonate solution was added to the reaction solution, which was then stirred for about 4 hours. 215 μL of a 50% (v/v) aqueous acetic acid solution were added to neutralize the reaction solution, after which 2.5 g of sodium chloride was added and stirred in. 400 ml of ethanol was added to precipitate the solution, and the precipitate was washed twice with an 85% (v/v) aqueous ethanol solution, twice with ethanol and twice with diethyl ether, and vacuum dried overnight at room temperature to obtain sodium hyaluronate with introduced aminoethanol-diclofenac (test substance). The diclofenac introduction rate as measured with a spectrophotometer was 18 mol %.

<Test Procedures>

The effectiveness of the investigational drug (test drug (composition for treating joint disease of invention) or placebo) when administered 3 times at four-week intervals in the knee joint cavities of human knee osteoarthritis patients was investigated by a multi-center collaborative, randomized, placebo-controlled, double-blind, parallel-group comparison trial. The test drug and placebo were as follows:

Test drug: 3 mL of aqueous solution for injection containing 30 mg of test substance (3.6 mg as diclofenac);

Placebo: 3 mL of aqueous solution for injection containing no test substance.

The total amount (3 mL) of the test drug or placebo was administered (injected) into the knee joint cavities of the affected knees of the target patients on week 0, week 4 and week 8 for a total of three injections.

The target patients were determined based on the following inclusion criteria 1 to 9 and exclusion criteria 1 to 23.

(Inclusion Criteria)

Patients fulfilling all of the inclusion criteria 1 to 9 below were targeted.

1. Patients diagnosed with knee OA according to the criteria of the American College of Rheumatology on the screening examination date (performed within two weeks before the initial administration date).

2. Patients having pain due to OA in the target knee beginning 12 weeks or more before the consent date.

3. Patients with a Kellgren and Lawrence (KL) grade of 2 or 3 in standing frontal X-ray image findings on the screening examination date. However, if X-ray images taken within 6 months before the beginning of screening are available, these images may be used as a substitute for images taken on the screening examination date.

KL grade 2: Mild OA. Micro-osteophyte formation, sometimes accompanied by narrowing of the joint space, bone hardening or bone cyst formation KL grade 3: Moderate OA. Osteophytes and moderate narrowing of the joint space.

4. Patients aged not less than 40 and not more than 75 on the consent date.

5. Patients having an average value of 5 WOMAC® A (pain) scores and a 50-foot walk test pain score of not less than 50 mm and not more than 90 mm in the target knee on the screening examination date and initial administration date.

6. Patients having an average value of 5 WOMAC® A (pain) scores and a 50-foot walk test pain score of not more than 30 mm in the non-target knee on the screening examination date and initial administration date.

7. Patients capable of walking without walking implement (cane, etc.) or assistance.

8. Patients able to discontinue the test drug and drug therapy other than acetaminophen in the target knee between the screening initiation date and the end of observation (use of acetaminophen is also prohibited beginning two days before hospital visit dates including screening)

9. Patients who have given written consent for participation in the trial based on free will after receiving sufficient explanation in writing and understanding its content.

(Exclusion Criteria)

Patients meeting any of the exclusion criteria 1 to 23 below were excluded from the trial.

1. Patients in whom the target knee clearly has secondary OA due to other conditions such as injury.

2. Patients having pain other than the target disease in the lower body that could affect the evaluation, or patients having OA of the lower body other than the knee (ankle OA, hip joint OA, etc.) on the screening examination date or initial administration date.

3. Patients having inflammatory disease, infection or the like of the target knee joint on the screening examination date or initial administration date, or patients who suffered from such a disease for a period falling within 1 year before the consent date.

4. Patients who have a skin disease or infection of the administration site on the screening examination date or initial administration date, and who are therefore at risk of infection from the injection.

5. Patients who have undergone surgical treatment or other invasive treatment (arthroscopy, joint washing, etc.) of the affected knee within one year before the initial screening date.

6. Patients who have taken the following drugs within seven days before the initial screening date. However, except for diclofenac and opioid analgesics, in the case of external preparations (other than suppositories) this applies only to those used on the lower limb on the same side as the target knee.

NSAIDs (may be used in combination with low-dose aspirin to prevent thrombosis)

Corticosteroid preparations
Opioid painkillers
Peripheral neuropathic pain remedies
Local anesthetic of the target knee
Chondroitin sulfate injection
Anticonvulsants, antidepressants, anxiety drugs and Oriental medicines used for purposes of pain relief 7. Patients who have received intraarticular administration of crosslinked sodium hyaluronate preparations (such as SYNVISC®) in the affected knee within six months before the initial screening date, or patients who have received intraarticular administration of sodium hyaluronate preparations (such as ARTZ® and SUVENYL®) in the affected knee within three months before screening.

8. Patients who have taken the following drugs within 28 days before the start of screening. However, in the case of external preparations (other than suppositories) this applies only to those used on the lower limb on the same side as the target knee.
Triamcinolone acetonide
Methylprednisolone acetic acid ester
Oxaprozin
Ampiroxicam
Piroxicam 9. Patients who have undergone block therapy (neural block, epidural block, facet joint block, etc.) within 28 days before the initial screening date.

10. Patients who have taken chondroitin sulfate (pharmaceutical products only) internally for relief of joint pain within 28 days before the initial screening date (patients who have been using it continuously since 29 days or more before the initial screening date may continue taking it during the trial).

11. Patients who have undergone physical therapy (exercise therapy, physical therapy, orthosis therapy) for treatment of the target knee OA within 28 days before the initial screening date (patients who have undergone such therapy continuously since 29 days or more before the initial screening date may continue it during the trial)

12. Patients with BMIs of 35.0 kg/m² or more on the screening examination date (or a date close to the initial administration date in the case of multiple measurements)

13. Women who are pregnant or nursing, or who are shown to be possibly pregnant as the result of a pregnancy test fa pregnancy test is performed on any woman who could be pregnant; testing is not required for any woman who could not be pregnant, such as those who have undergone a hysterectomy or bilateral tubal ligation or who appear to have gone through menopause (two months or more since last menstrual period).

14. Patients who have not agreed to appropriate birth control between the consent date and the end of observation 15. Patients suffering from or with a history of aspirin asthma (asthma attacks induced by NSAIDs or the like)

16. Patients having a history of hypersensitivity to sodium hyaluronate, diclofenac sodium or acetaminophen 17. Patients with a history of (within five years of consent date) or complications of malignant tumors. However, those who have been judged to be cured by surgical treatment or local therapy may participate.

18. Patients having any of the following symptoms or conditions which may affect the results of the trial:
Patients having severe heart disease, liver disease, kidney disease, blood disease or immunodeficiency
Patients having systemic joint disease such as rheumatoid arthritis or gout
Patients having systemic chronic pain disorders such as fibromyalgia
Patients having peripheral neuropathy due to diabetes or the like 19. Patients having a history or complications of drug addict ion or alcoholism 20. Patients who fail into any of the following categories in clinical examination on the screening examination date:
Patients with AST or ALT levels at least 2.5 times the maximum reference value of the measuring institution
Patients with serum creatinine at least 1.5 times the maximum reference value of the measuring institution
Patients who test positive for hepatitis C antibodies or Hepatitis B surface antigen.

21. Patients who have participated in trials of the test substance in the past

22. Patients who have participated in trials of other drugs or medical equipment within 16 weeks before the consent date 23. Other patients whom the investigative physician or clinical trial physician has judged to be unsuitable for participation in the trial The target patients for administration were determined based on inclusion criteria 1 to 0 and exclusion criteria 1 to 23 above.

A total of 176 patients who were found to meet the inclusion criteria and exclusion criteria were separated randomly .into a test drug administration group (87 subjects) and a placebo administration group (89 subjects).

[Table 1] below shows the results of a breakdown of each patient group using a SMI of 25 kg/m² and pain duration periods (DP) of 26 weeks as threshold values.

The numbers of patients in Table 1 below correspond to patient numbers at the start of testing.

Effectiveness was evaluated by the following evaluation methods at the time of the initial administration and at evaluation points 1, 2, 4, 6, 8, 10 and 12 weeks after the initial administration.

<Evaluation Methods>

Effectiveness was evaluated using the WOMAC® evaluation (The Journal of Rheumatology 1988; 15:12, p. 1833-1840) developed by Dr. Nicholas Bellamy. The WOMAC(r) evaluation has been established as a method for evaluating osteoarthritis (The Journal of Rheumatology 2000; 27:11, p. 2635-2641).

The patient response method used the VAS (Visual Analog Scale). With the VAS, the degree of a patient's own feelings in response to each question is indicated by the patient on a 100 mm line, and the degree is evaluated according to the position on the line. Position is represented as length from the left end of the scale. For example, a patient is asked the same question about pain in evaluations before and after administration, and the patient responds by indicating a position (degree) on the scale. Numerical values for improvement are then obtained based on the difference between the length indicated by the patient before administration (baseline) and the length indicated by the patient during each evaluation after administration.

<Results>

The improvement effects were quantified based on the difference between the length indicated by the patient before administration (baseline) and the length indicated by the patient at the time of each evaluation after administration. The analysis results for questions about pain (WOMAC® A: evaluates intensity of pain during walking, etc.) are shown in Table 1 below. In the table, the lower the value of the change difference below 0, the greater the improvement effect.

The priority claim for this application is based on Japanese Patent Application No. 2017-49204 submitted to the Japanese Patent Office on Mar. 14, 2017 and on Japanese Patent Application No. 2017-132510 submitted to the Japanese Patent Office on Jul. 6, 2017, and the entire contents of those applications are incorporated by reference into this application.

TABLE 1

| WOMAC-A | | Placebo group | | | | Test Drug Group | | | | Test Drug Group vs. Placebo Group | | | |
|---|---|---|---|---|---|---|---|---|---|---|---|---|---|
| | | Number of patients | Change | Lower 95% CL* | Upper 95% CL | Number of patients | Change | Lower 95% CL | Upper 95% CL | Change difference | P value | Lower 95% CL | Upper 95% CL |
| Whole group | | 89 | −21.7 | −25.9 | −17.5 | 87 | −28.7 | −32.9 | −24.5 | −7.0 | 0.018 | −12.7 | −1.2 |
| BMI (kg/m²) | <25 | 47 | −23.1 | −29.0 | −17.2 | 40 | −25.2 | −31.1 | −19.3 | −2.1 | 0.602 | −10.2 | 5.9 |
| | 25≤ | 42 | −19.1 | −25.3 | −12.9 | 47 | −32.6 | −38.7 | −26.5 | −13.4 | 0.003 | −22.0 | −4.9 |
| DP (week) x BMI | BMI <25 and/or DP < 26 | 55 | −24.1 | −29.9 | −18.3 | 49 | −27.2 | −32.9 | −21.6 | −3.2 | 0.416 | −10.8 | 4.5 |
| | 25 ≤ BMI and 26 ≤ DP | 34 | −17.0 | −23.1 | −10.8 | 38 | −30.7 | −36.6 | −24.7 | −13.7 | 0.002 | −22.2 | −5.2 |

*CL = Confidence limit
Change: Average value of change from baseline value (measured before start of administration) 12 weeks after initial administration. Estimated by mixed model for repeated measure (MMRM) analysis using the test group, evaluation point, interaction between test group and evaluation point, baseline value and KL grade as fixed effects (Correlation structure: unstructured; Degree of freedom: Kenward-Roger Method).
Change difference: Change value of test drug group minus change value of placebo group
DP: Duration of pain (weeks)

As shown above, it was found that chronic osteoarthritis could be improved dramatically in comparison with the placebo group by administering the composition for treating joint disease of the invention (test drug) (change difference: −7.0).

In the test drug group, a certain degree of improvement in osteoarthritis was seen even in patients with BMIs of less than 25 kg/m² (change difference: −2.1).

However, in patients with BMIs of at least 25 kg/m² in the test drug group there was an especially dramatic improvement effect in osteoarthritis in comparison with the placebo group (change difference: −13.4). Even compared with the results for the test drug group as a whole, a greater improvement effect was seen in the test drug group consisting of patients with BMIs of at least 25 kg/m².

Of the patients with BMIs of at least 25 kg/m², an extremely great improvement effect in osteoarthritis in the test group in comparison with the placebo group was seen in those with pain duration periods of at least 26 weeks.

These analysis results were for pain (WOMAC® A), but a similar improvement tendency was observed in a physical function evaluation (WOMAC® C: evaluated based on difficulty with activities of daily living such as climbing stairs and getting in and out of automobiles).

<Conclusions>

The composition for treating joint disease of the invention exhibited a significant improvement effect against joint disease of human joint disease patients. A particularly dramatic improvement effect was found in human joint disease patients with BMIs of at least 25 kg/m², and particularly in patients with BMIs of not less than 25 kg/m² and less than 35 kg/m². An extremely great improvement effect was seen in patients with long pain duration periods of at least DP 26 weeks before the initial administration and with BMIs of at least 25 kg/m².

The present invention was described in detail using specific examples and various embodiments, but a person skilled in the art can easily understand that many modifications and applications of the embodiments described in this Description are possible as long as they do not deviate from the spirit and scope of the invention.

INDUSTRIAL APPLICABILITY

The present invention is industrially applicable in the pharmaceutical industry and the like because it provides a composition for treating joint disease having a significant effect against joint disease in human joint disease patients, together with a method for using this composition for treating joint disease to treat human joint disease.

The invention claimed is:

1. A method for treating a human joint disease, comprising:
    administering a composition comprising a modified hyaluronic acid or a pharmaceutically acceptable salt thereof having a group of a steroidal or non-steroidal anti-inflammatory compound, for use in a joint disease patient having a BMI of at least 25 kg/m² and less than 35 kg/m²,
    wherein the composition is an injection, and
    wherein the steroidal or non-steroidal anti-inflammatory compound is diclofenac or a pharmaceutically acceptable salt thereof.

2. The method according to claim 1, wherein the joint disease patient having duration of pain for 26 weeks or more.

3. The method according claim 1, wherein the group of an anti-inflammatory compound is bonded to a hyaluronic acid or a pharmaceutically acceptable salt thereof via a spacer in the modified hyaluronic acid or a pharmaceutically acceptable salt thereof.

4. The method according to claim 3, wherein the mode of bonding between the hyaluronic acid or a pharmaceutically acceptable salt thereof and the spacer is selected from the group consisting of amide bond, ether bond, ester bond, thioester bond and sulfide bond.

5. The method according to claim 3, wherein the mode of bonding between the spacer and the group of an anti-inflammatory compound is selected from the group consisting of amide bond, ether bond, ester bond, thioester bond and sulfide bond.

6. The method according to claim 1, wherein the group of an anti-inflammatory compound is covalently bonded to a hyaluronic acid skeleton via a spacer having a structure of the following Formula (1):

—NR$^1$—R$^2$—O-  (1)

in Formula (1), R$^1$ is a hydrogen atom or a alkyl group having carbon number of 1 to 3; and R$^2$ is an optionally substituted linear alkylene group having carbon number of 1 to 12.

7. The method according to claim 6, wherein R$^1$ is a hydrogen atom and R$^2$ is an ethylene group.

8. The method according to claim 1, wherein the modified hyaluronic acid or a pharmaceutically acceptable salt thereof contains a structural unit of the following Formula (2):

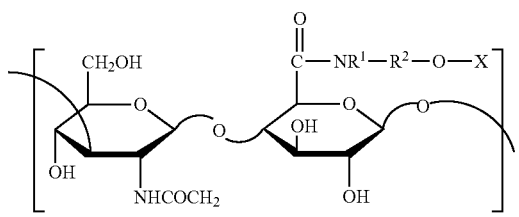

in Formula (2), R$^2$ is a hydrogen atom or a alkyl group having carbon number of 1 to 3; R$^2$ is an optionally substituted linear alkylene group having carbon number of 1 to 12; and X is the group of an anti-inflammatory compound.

9. The method according to claim 8, wherein 1e is a hydrogen atom and R$^2$ is an ethylene group.

10. The method according to claim 8, wherein the percent ratio of the number of structural units of the Formula (2) to the total number of constituent disaccharide units constituting the modified hyaluronic acid or a pharmaceutically acceptable salt thereof is not less than 0.1 mol % and not more than 80 mol %.

11. The method according to claim 1, wherein a dose of not less than 5 mg and not more than 100 mg by weight of the modified hyaluronic acid or a pharmaceutically acceptable salt thereof is administered in a single administration.

12. The method according to claim 1, wherein a dose of not less than 0.1 mg and not more than 20 mg by weight of the anti-inflammatory compound is administered in a single administration.

13. The method according to claim 1, wherein the joint disease is osteoarthritis.

14. The method according to claim 1, wherein the treatment consists in at least one selected from the group consisting of improving, curing, and suppressing the progress of symptoms.

15. The method according to claim 14, wherein the treatment consists in improving, curing or suppressing the progress of joint pain, or improving joint function.

16. The method according to claim 1, wherein the composition further comprises a pharmaceutically acceptable carrier.

* * * * *

UNITED STATES PATENT AND TRADEMARK OFFICE
CERTIFICATE OF CORRECTION

PATENT NO. : 10,925,839 B2
APPLICATION NO. : 16/492365
DATED : February 23, 2021
INVENTOR(S) : Kazuyuki Kano et al.

It is certified that error appears in the above-identified patent and that said Letters Patent is hereby corrected as shown below:

In the Specification

Column 2, Line 29, "EMI" should be replaced with -- "BMI" --.

Column 2, Line 42, "present," should be replaced with -- present --.

Column 3, Line 19, "or." should be replaced with -- or --.

Column 3, Line 56, "should," should be replaced with -- should --.

Column 3, Line 62, "salt," should be replaced with -- salt --.

Column 3, Line 67, "metal," should be replaced with -- metal --.

Column 4, Line 59, "individual," should be replaced with -- individual --.

Column 4, Lines 60, "combination," should be replaced with -- combination --.

Column 5, Line 25, "from," should be replaced with -- from --.

Column 7, Lines 27, "that," should be replaced with -- that --.

Column 8, Line 48, "methionodide)," should be replaced with -- methiodide), --.

Column 8, Line 50, "N-hydrozybenzotriazole" should be replaced with -- N-hydroxybenzotriazole --.

Column 9, Line 55, "Description," should be replaced with -- Description. --.

Column 9, Line 58, "pal/nitate" should be replaced with -- palmitate --.

Signed and Sealed this
Eighteenth Day of May, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 10,925,839 B2

Column 9, Line 66, "etodoiac," should be replaced with -- etodolac, --.

Column 10, Line 1, "rnofezolac," should be replaced with -- mofezolac, --.

Column 10, Line 3, "raeloxicam," should be replaced with -- meloxicam, --.

Column 10, Line 8, "aluminoprofen," should be replaced with -- alminoprofen, --.

Column 10, Line 15, "salsaiate," should be replaced with -- salsalate, --.

Column 10, Line 20, "lefiunomide," should be replaced with -- leflunomide, --.

Column 10, Line 23, "tocilizurnab)" should be replaced with -- tocilizumab) --.

Column 10, Line 28, "acematacin," should be replaced with -- acemetacin, --.

Column 10, Line 31, "aluminoprofen," should be replaced with -- alminoprofen, --.

Column 10, Line 33, "salsaiate," should be replaced with -- salsalate, --.

Column 12, Line 12, "3" should be replaced with -- 8 --.

Column 13, Line 53, "joint," should be replaced with -- joint --.

Column 15, Line 16, "[3]" should be replaced with -- [5] --.

Column 16, Line 2, "30" should be replaced with -- 80 --.

Column 16, Line 19, "Improving" should be replaced with -- improving --.

Column 16, Line 39, "joint," should be replaced with -- joint --.

Column 17, Line 47, "30" should be replaced with -- 80 --.

Column 18, Line 22, "[4]" should be replaced with -- [44] --.

Column 18, Line 22, "joint," should be replaced with -- joint --.

Column 18, Line 30, "leas" should be replaced with -- less --.

Column 18, Line 50, "300,000," should be replaced with -- 800,000, --.

Column 18, Line 55, "dissolved," should be replaced with -- dissolved --.

Column 18, Line 55, "dichl or cinethane" should be replaced with -- dichloromethane --.

CERTIFICATE OF CORRECTION (continued)
U.S. Pat. No. 10,925,839 B2

Column 21, Line 46, "fa" should be replaced with -- of a --.

Column 22, Line 7, "fail" should be replaced with -- fall --.

Column 22, Line 24, "0" should be replaced with -- 9 --.

Column 22, Line 28, ".into" should be replaced with -- into --.

In the Claims

Column 24, Line 56, Claim 3 "according" should be replaced with -- according to --.

Column 25, Line 14, Claim 7 "R1is" should be replaced with -- R1 is --.

Column 26, Line 4, Claim 9 "le" should be replaced with -- R1 --.